(12) United States Patent
Veening et al.

(10) Patent No.: US 11,959,867 B2
(45) Date of Patent: Apr. 16, 2024

(54) SMART VESSEL AND FILLING STATION WITH PRODUCT QUALITY MONITORING AND ALERTS

(71) Applicant: Diversey, Inc., Fort Mill, SC (US)

(72) Inventors: Jan Eduard Veening, Ijsselstein (NL); Lambertus Gerardus Petrus van der Heijden, Bunnik (NL); David Holden, Utrecht (NL); Arnoud Gengler, De Wijk (NL)

(73) Assignee: Diversey, Inc., Fort Mill, SC (US)

( * ) Notice: Subject to any disclaimer, the term of this patent is extended or adjusted under 35 U.S.C. 154(b) by 768 days.

(21) Appl. No.: 17/049,389

(22) PCT Filed: Apr. 25, 2019

(86) PCT No.: PCT/US2019/029095
§ 371 (c)(1),
(2) Date: Oct. 21, 2020

(87) PCT Pub. No.: WO2019/210048
PCT Pub. Date: Oct. 31, 2019

(65) Prior Publication Data
US 2021/0255129 A1 Aug. 19, 2021

Related U.S. Application Data

(60) Provisional application No. 62/662,960, filed on Apr. 26, 2018.

(51) Int. Cl.
*G01N 27/06* (2006.01)
*B01L 3/00* (2006.01)
*G01P 13/00* (2006.01)

(52) U.S. Cl.
CPC .............. *G01N 27/06* (2013.01); *B01L 3/508* (2013.01); *G01P 13/00* (2013.01); *B01L 2300/023* (2013.01); *B01L 2300/0627* (2013.01)

(58) Field of Classification Search
CPC ... G01N 27/06; B01L 3/508; B01L 2300/023; B01L 2300/0627; G01P 13/00;
(Continued)

(56) References Cited

U.S. PATENT DOCUMENTS 5,802,015 A 9/1998 Rothschild et al.
5,922,606 A 7/1999 Jenkins et al.
(Continued)

FOREIGN PATENT DOCUMENTS

CA 2717631 A1 4/2012
CN 106031698 10/2016
(Continued)

OTHER PUBLICATIONS

Meade LT, Rushton WE. Optimizing insulin pump therapy: a quality improvement project. Diabetes Educ. Nov.-Dec. 2013;39(6):841-7. doi: 10.1177/0145721713504628. Epub Sep. 17, 2013. PMID: 24045332. (Year: 2013).*
(Continued)

*Primary Examiner* — Eric S. McCall
*Assistant Examiner* — Timothy P Graves
(74) *Attorney, Agent, or Firm* — Lorenz & Kopf, LLP (57) ABSTRACT

A vessel includes a memory and a processor operatively coupled to the memory. The memory is configured to store a vessel identifier. The processor is configured to initiate a timer for a shelf life of a solution placed into the vessel. The processor is also configured to conduct a measurement of the solution using one or more sensors in the vessel. The processor is also configured to compare the measurement to
(Continued)

a threshold for the solution. The processor is further configured to activate a solution indicator to indicate that the solution should be discarded responsive to a determination that the shelf life has expired or a determination that the measurement exceeds the threshold.

14 Claims, 6 Drawing Sheets (58) Field of Classification Search
CPC . A61L 2/18; A61L 2/22; B05B 12/004; B05B 11/0027; B05B 11/1059; B65D 83/56; G08B 21/245
See application file for complete search history.

(56) References Cited

U.S. PATENT DOCUMENTS

| | | | |
|---|---|---|---|
| 6,595,250 | B1 | 7/2003 | Paulus |
| 7,008,523 | B2 | 3/2006 | Herrington |
| 7,424,399 | B2 | 9/2008 | Kahn et al. |
| 7,900,658 | B2 | 3/2011 | Osborne et al. |
| 8,550,288 | B2 | 10/2013 | Briar et al. |
| 9,051,163 | B2 | 6/2015 | Mehus et al. |
| 9,573,171 | B2 | 2/2017 | Shanahan et al. |
| 2002/0139840 | A1* | 10/2002 | Madrid .................. B65D 79/02 235/375 |
| 2004/0124988 | A1 | 7/2004 | Leonard et al. |
| 2011/0042202 | A1 | 2/2011 | Pettee et al. |
| 2011/0100506 | A1 | 5/2011 | Zabuludovsky-Nerubay |
| 2013/0103463 | A1* | 4/2013 | Briar .................... B65D 25/02 340/815.4 |
| 2013/0199928 | A1 | 8/2013 | Reinders et al. |
| 2014/0368318 | A1 | 12/2014 | Paris et al. |
| 2016/0030683 | A1* | 2/2016 | Taylor .................. A61M 5/345 604/151 |
| 2016/0184851 | A1 | 6/2016 | McNulty et al. |
| 2017/0022045 | A1 | 1/2017 | Ray et al. |
| 2017/0158389 | A1 | 6/2017 | Lavelock |
| 2017/0304475 | A1 | 10/2017 | Frische et al. |

FOREIGN PATENT DOCUMENTS

| | | |
|---|---|---|
| CN | 106031698 A | 10/2016 |
| CN | 106511099 A | 3/2017 |
| CN | 107835712 A | 3/2018 |
| EP | 2967506 | 1/2016 |
| EP | 2079647 B1 | 5/2017 |
| EP | 2404193 B1 | 5/2017 |
| GB | 2550232 | 11/2017 |
| WO | WO 2007/148080 | 12/2007 |
| WO | WO 2014/102556 | 7/2014 |
| WO | WO2017/045902 | 3/2017 |

OTHER PUBLICATIONS

Zisser HC. The OmniPod Insulin Management System: the latest innovation in insulin pump therapy. Diabetes Ther. Aug. 2010;1(1):10-24. doi: 10.1007/s13300-010-0004-6. Epub Sep. 13, 2010. PMID: 22127670; PMCID: PMC3118276. (Year: 2010).*
First Office Action for CN201980043315.5, dated Dec. 28, 2021, English translation provided.
International Search Report and Written Opinion for PCT/US2019/029095, dated Aug. 2, 2019.
Office Action issued for CN patent application 201980043315.5 dated Aug. 23, 2022; pp. 1-25.
Extended European Search Report issued on EP19792428.5, dated May 21, 2021.

* cited by examiner

SMART VESSEL AND FILLING STATION WITH PRODUCT QUALITY MONITORING AND ALERTS

CROSS-REFERENCE TO RELATED APPLICATION

This application is a National Stage of International Application No. PCT/US19/29095, filed Apr. 25, 2019, which claims the benefit of U.S. Patent Application No. 62/662,960, filed Apr. 26, 2018, the contents of which are herein incorporated by reference.

BACKGROUND

Cleaning and disinfectant solutions are used around the world to clean floors, tables, countertop surfaces, desks, machinery, tools, etc. to help prevent the spread of diseases, germs, and other microorganisms. These solutions typically include one or more chemicals that are designed to kill the microorganisms upon contact. The solutions can be formed by diluting the concentrated chemical(s) with water to an appropriate concentration for the application, by using electrolysis or other chemical generation process, or as a ready to use concentration produced by a factory. The dilution (or electrolysis) process is controlled to ensure that the solution has the correct (regulatory compliant) efficacy level, to ensure that the solution is safe to use around humans and animals, and to protect the user and the environment in the event of a spill.

SUMMARY

An illustrative vessel includes a memory and a processor operatively coupled to the memory. The memory is configured to store a vessel identifier. The processor is configured to initiate a timer for a shelf life of a solution placed into the vessel. The processor is also configured to conduct a measurement of the solution using one or more sensors in the vessel. The processor is also configured to compare the measurement to a minimum chemistry concentration threshold for the solution. The processor is further configured to activate a solution indicator to indicate that the solution should be discarded responsive to a time determination that the shelf life has expired or a quantitative or qualitative determination that the measurement exceeds the minimum chemistry concentration threshold.

An illustrative vessel system includes a filling station and a vessel. The filling station includes a filling station transceiver configured to receive a vessel identifier from the vessel. The filling station also includes a filling station processor operatively coupled to the filling station transceiver. The filling station processor is configured to conduct a first reference measurement on water used to form a solution using one or more filling station sensors. The filling station processor is also configured to conduct a second reference measurement on the solution prior to placement of the solution in the vessel using the one or more filling station sensors. The filling station processor is also configured to cause the filling station transceiver to transmit data regarding the first reference measurement and the second reference measurement to the vessel. The filling station processor is further configured to cause a fill nozzle of the filling station to dispense the solution into the vessel. The vessel includes a vessel memory configured to store the vessel identifier. The vessel also includes a vessel transceiver configured to transmit the vessel identifier to the filling station and to receive the data regarding the first reference measurement and the second reference measurement. The vessel further includes a vessel processor operatively coupled to the vessel memory and the vessel transceiver. The vessel processor is configured to initiate a timer for a shelf life of the solution placed into the vessel. The vessel processor is also configured to conduct a measurement of the solution using one or more vessel sensors. The vessel processor is also configured to compare the measurement to a threshold for the solution. The vessel processor is further configured to activate a solution indicator to indicate that the solution should be discarded responsive to a determination that the shelf life of the timer has expired or that the measurement exceeds the threshold.

Other principal features and advantages of the invention will become apparent to those skilled in the art upon review of the following drawings, the detailed description, and the appended claims.

BRIEF DESCRIPTION OF THE DRAWINGS

Illustrative embodiments will hereafter be described with reference to the accompanying drawings, wherein like numerals denote like elements. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

As discussed above, traditional cleaning and disinfecting solutions often include one or more chemicals that are diluted with a liquid such as water. The dilution process, which often involves mixing the chemical(s) with liquid (e.g., water) and placing them into a vessel, can be performed at a factory that produces the solution or by an end user at home or work. Electrolysis can also be used to form a dilute solution at a filling station such as an electrochemical activation (ECA) dispensing machine. Once placed into a vessel, the quality of the solution can degrade due to a number of causes such as natural chemical decay, ultraviolet (UV) light exposure, contamination, impurities in the water or other liquid used as a dilute, bacterial growth in the solution (e.g., in a cleaning solution), the passage of time, etc. This quality degradation eventually renders the solution unfit for its intended purpose and can result in ineffective cleaning and disinfection, and therefore the unintended growth and spreading of bacteria, germs, dirt, etc. This problem is exacerbated because most customers are unaware of the shelf life of the solutions that they make/use, and therefore do not know when the solution will go bad. Additionally, customers typically do not monitor the solution age once it is made or purchased (e.g., as a ready to use solution produced in a factory) and oftentimes will top off an old solution with a new solution to fill a partially full vessel.

Figure 1:
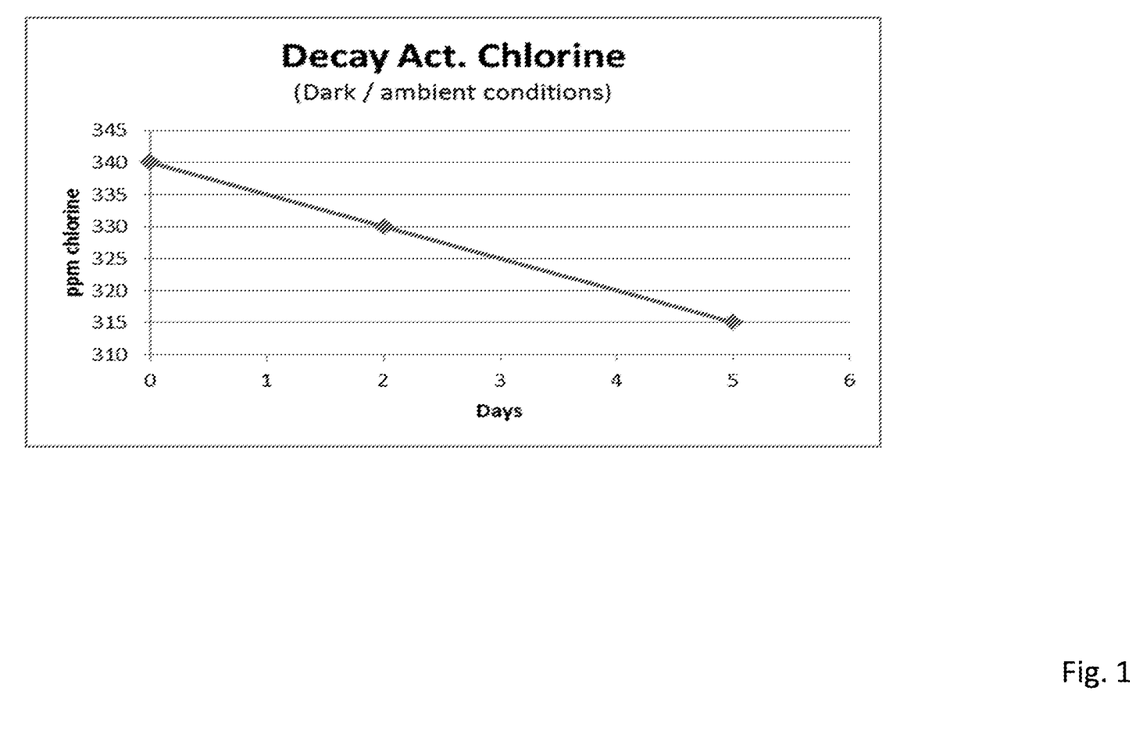
FIG. 1 depicts the decay of a chlorine solution over time in dark ambient conditions.

FIG. 1 depicts the decay of a chlorine solution over time in dark ambient conditions. It can be seen that the chlorine in the solution decays from 340 parts per million (ppm) to 315 ppm over 5 days, which represents over a 7% reduction in the active chlorine present in the solution. The decay of chlorine can become even more significant as more time passes and when the solution is placed in environments that have extreme temperatures, UV exposure, etc., until the point when the solution is no longer able to act as a suitable disinfecting solution. Unfortunately, traditional vessel systems do not monitor a solution that has been placed into a vessel, and are unable to alert a user that the solution is no longer able to perform its function. Traditional vessel systems also have no accurate way to help ensure that the cleaning, disinfecting, etc. solution is always applied at a required quality level and quantity.

Described herein is a vessel system that is able to monitor the quality of a solution within a vessel. The vessel can be a spray bottle, a squeeze bottle, a bucket, an applicator bottle or tube, a flask, or any other container in which the solution is stored prior to its application. The solution can include any type of cleaning solution, disinfectant solution, oxidizer solution, non-oxidizer solution, etc. known in the art. In an illustrative embodiment, the solution is created by dilution of one or more product concentrates or an electrolysis process.

In another illustrative embodiment, the vessel systems described herein include an intelligent (or smart) vessel that is filled using a filling station, such as an ECA dispensing machine. Upon being docked at the filling station, the vessel can be configured to communicate with the filling station such that the filling station is able to identify the vessel and ensure that the appropriate solution is added to the vessel. The filling station is also used to ensure that the vessel is empty prior to being filled to help ensure that a newly added solution is not degraded by any old solution remaining in the vessel. The filling station can also be used to test the concentration and quality of the chemical concentrate(s) and dilute(s) prior to their placement in the vessel and again after the solution is formed in the vessel. In an alternative embodiment, the vessel system may include a vessel that is filled with a hand mixed solution or a solution that is premixed at a factory.

As discussed in more detail below, the vessel is configured to store information regarding the solution that is received from the filling station. The vessel is also configured to use a timer to monitor the length of time that the solution has been in the bottle. Once a predetermined amount of time (i.e. shelf life) has passed, the vessel can activate an alarm and/or indicator to alert the user that it is time to replace the solution. The predetermined amount of time can be based on the type of solution, the concentration of the solution, the intended use of the solution, and/or the environmental conditions to which the solution will be subjected. The vessel can also be configured to periodically monitor the concentration of the solution and to alert the user if the concentration falls below a predetermined threshold. The concentration threshold can also be based on the type of solution, the concentration of the solution, the intended use of the solution, and/or the environmental conditions to which the solution will be subjected. The vessel can also include a motion sensor which can be used for the purposes of monitoring solution use and identifying the appropriate time to activate an alert/indicator for the user.

Figure 2:
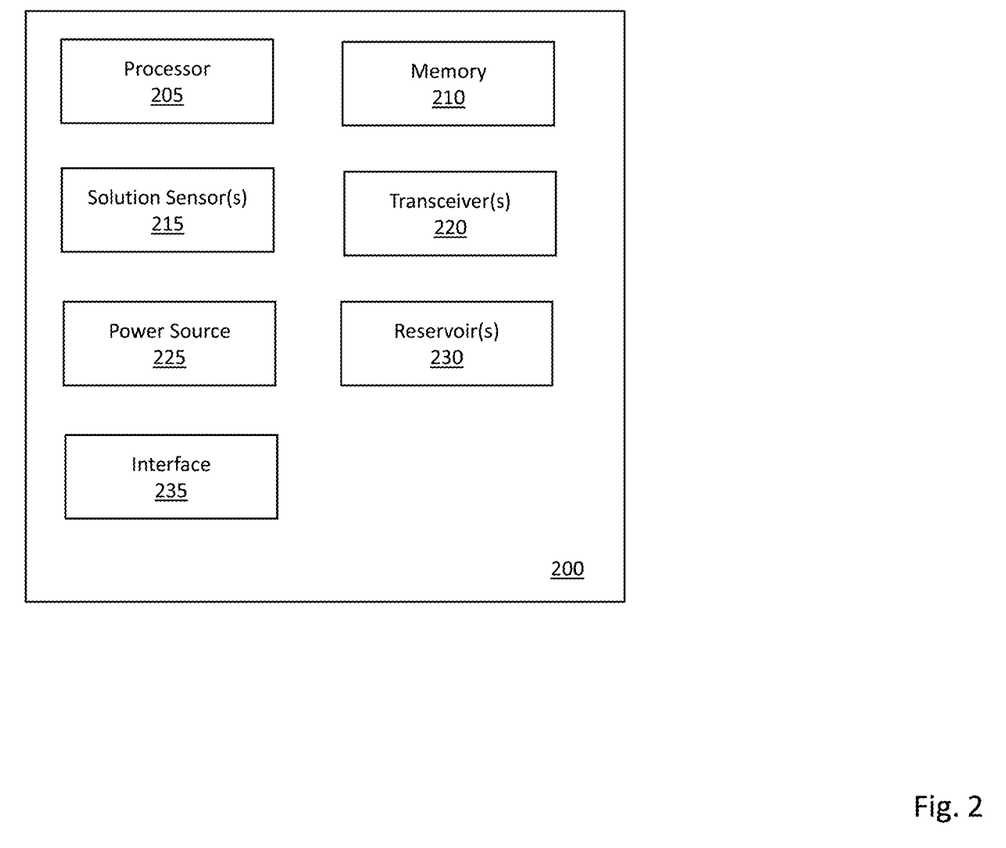
FIG. 2 is a block diagram of a filling station in accordance with an illustrative embodiment.
Figure 3:
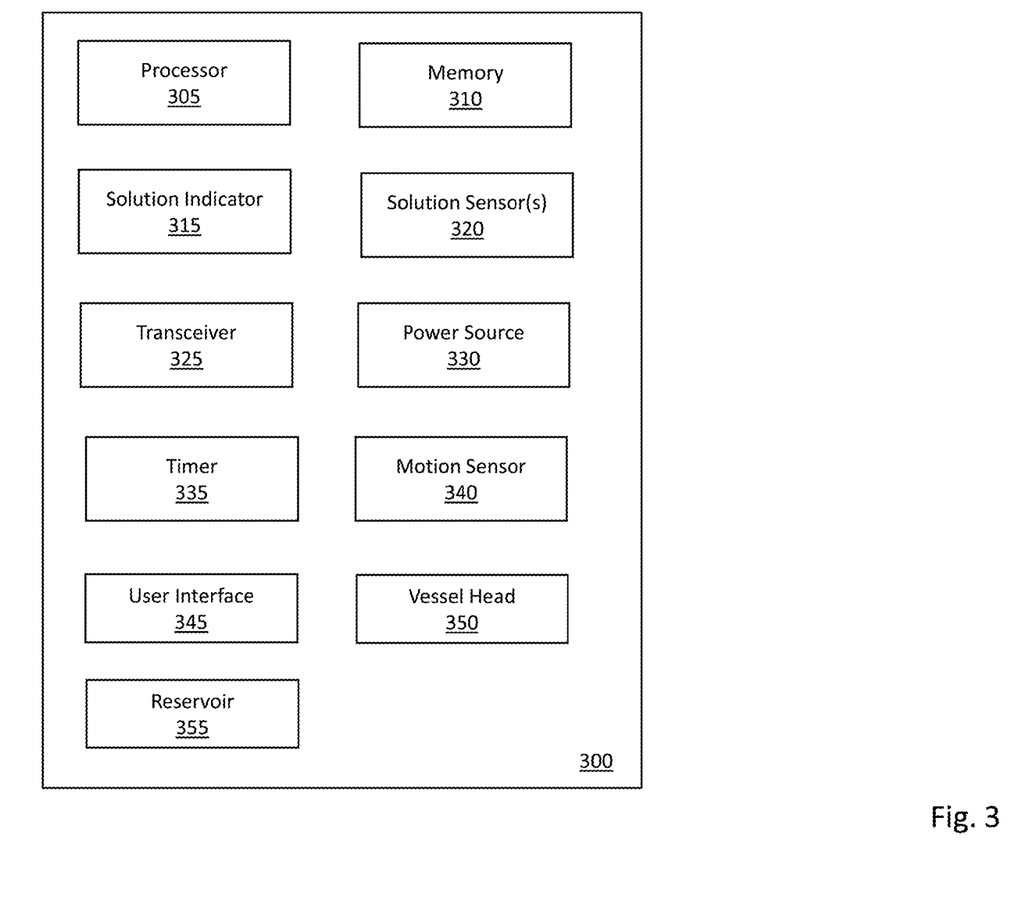
FIG. 3 is a block diagram of a vessel in accordance with an illustrative embodiment.

FIG. 2 is a block diagram of a filling station 200 in accordance with an illustrative embodiment. The filling station 200 includes a processor 205, a memory 210, solution sensor(s) 215, one or more transceivers 220, a power source 225, one or more reservoirs 230, and an interface 235. FIG. 3 is a block diagram of a vessel 300 in accordance with an illustrative embodiment. The vessel 300 includes a processor 305, a memory 310, a solution indicator 315, solution sensor(s) 320, a transceiver 325, a power source 330, a timer 335, a motion sensor 340, a user interface 345, a vessel head 350, and a reservoir 355. In alternative embodiments, the filling station 200 and the vessel 300 can include additional, fewer, and/or different components.

Referring to FIG. 2, the memory 210 of the filling station 200 can be any type of computer memory or storage known in the art. The memory 210 can be used to store vessel identifiers associated with specific vessels, a type of solution associated with each of the vessel identifiers, a shelf life for each type and/or concentration of solution, sensor data generated for a solution placed into a vessel, communication and other algorithms, etc.

The processor 205 of the filling station 200 can be any type of single or multiple computer processor known in the art. The processor 205 can be used to implement any algorithms stored in the memory 210, to control the one or more transceivers 220 to communicate with a vessel, to control the solution sensor(s), to generate instructions and/or thresholds for the vessel, and to control other components of the filling station 200. The one or more transceivers 220 can be any type of receiver(s) and transmitter(s) known in the art, and can be used to allow the filling station 200 to communicate with a vessel and/or a user device. In an illustrative embodiment, the one or more transceivers 220 are near-field communication (NFC) transceivers that are configured to transmit/receive data over a short distance using the NFC protocol. In alternative embodiments, additional and/or different transceiver types may be incorporated into the filling station 200 such as Bluetooth®, wi-fi, cellular, radio frequency (RF), etc.

The power source 225 of the filling station 200 can be a standard electrical outlet, a battery, and/or any other type of charge storage/distribution components known in the art. The power source 225 is used to provide power to the processor 205 and other components of the filling station 200. The one or more reservoirs 230 of the filling station 200 are used to store a dilute, one or more chemicals that are mixed with the dilute, and/or a formed solution. In one embodiment, the filling station 200 can be configured to generate solutions using electrochemical processes known in the art, such as electrolysis.

The interface 235 of the filling station 200 can include a touchscreen display, a keyboard, one or more dispensing buttons, and/or any other components that allow a user to interact with the filling station 200. In one embodiment, users can also interact with the filling station 200 through an application on a user device such as a smart phone, computer, etc.

The one or more solution sensor(s) 215 can be one or more electrical sensors that are used to monitor temperature, conductivity, amperage, resistance, and/or voltage of a solution. In an illustrative embodiment, the solution sensor(s) 215 are used to determine characteristics of the components (e.g., cleaning/disinfection chemistry, water, and contaminants in the water which may affect the accuracy of the filling station sensors) which form the solution and the solution itself prior to its initial placement into a vessel. In an illustrative embodiment, the filling station 200 is designed to only fill a vessel that is determined to be empty such that new solution is not degraded by any old solution remaining in the vessel.

In another illustrative embodiment, the types of measurements performed on a solution using the solution sensor(s) 215 can depend on the type of solution. For example, based on its composition, a cleaning solution is less likely to experience chemical degradation than a disinfecting solution. However, cleaning solutions are more likely to experience biological growth (e.g., bacteria) and contamination than a disinfecting solution. As a result, in one embodiment, a cleaning solution may be monitored solely based on a shelf life, which is a period of time during which the solution is expected to be effective for its intended use. Conversely, a disinfecting solution may be monitored to periodically determine one or more chemical concentrations in the solution to determine if the solution is still effective or if it should be replaced. In other embodiments, a cleaning solution and a disinfecting solution can both be subjected to shelf life monitoring and chemical concentration monitoring. A more detailed discussion of the solution monitoring processes is included below, along with several examples.

Referring now to FIG. 3, the memory 310 of the vessel 300, which can be any type of computer memory or storage known in the art, can be used to store information such as a vessel identifier (ID), data regarding the type and content of the solution stored in the vessel, solution testing algorithms, shelf life data, communication algorithms, and/or any other relevant information that allows the vessel 300 to properly function.

The processor 305 can be any type of single or multiple computer processor known in the art. The processor 305 can be used to implement the algorithms stored in the memory 310, to control the transceiver 325 to communicate with a filling station or user device, to process data received from the solution sensor(s) 320 and the motion sensor 340, to control the solution indicator 315, etc. The transceiver 325 can be any type of transmitter and receiver known in the art. In an illustrative embodiment, the transceiver 325 is a near-field communication (NFC) transceiver that is configured to transmit/receive over a short distance using the NFC protocol. In alternative embodiments, additional and/or different transceiver types may be incorporated into the vessel 300, such as Bluetooth®, wi-fi, cellular, radio frequency (RF), etc.

The power source 330 of the vessel 300 can be a battery or any other type of portable charge storing component known in the art. The power source 330 can be used to provide power to all of the other components of the vessel 300. In one embodiment, the power source 330 can be rechargeable such that a user is able to recharge the power source 330 at a filling station or a standard power outlet.

The timer 335 is used to monitor the amount of time that a solution has been in the vessel 300. In an illustrative embodiment, the timer 335 is reset when the solution is placed into the vessel 300. The timer 335 can be reset by the filling station used to fill the vessel 300, by the processor 305 of the vessel 300 in response to an instruction received from the filling station, or by a user of the vessel 300. Once a predetermined amount of time indicative of the shelf life of the solution passes on the timer 335, the processor 305 can activate the solution indicator 315 such that the user is made aware that the solution needs to be replaced. The predetermined amount of time (shelf life) can be stored in the memory 310 and can be specific to the type of solution, the original concentration of the solution, the intended use of the solution, and/or the ambient conditions in which the solution is used/stored. The predetermined amount of time can be calculated using any procedures known in the art.

The one or more solution sensor(s) 320 can include one or more electrical sensors that are used to monitor temperature, conductivity, amperage, resistance, and/or voltage such that the concentration of the cleaning or disinfection chemicals can be monitored in the solution. In one embodiment, the vessel 300 can include the same type(s) of solution sensors as the filling station 200. Alternatively, the vessel 300 may include different solution sensors than the filling station 200. The one or more solutions sensor(s) 320 can be used to determine whether the vessel is empty as described herein. Use of the solution sensor(s) 320 to perform solution monitoring is also described in more detail in the examples included below.

The solution indicator (or alarm) 315 can include one or more lights such as light-emitting diodes (LEDs), a display that includes text or symbols, one or more sound generating components, one or more vibration generating components, and/or any other components that can be used to alert a user of the status of a solution in the vessel 300. In one embodiment, the solution indicator 315 can be in the form of a light that is green when the solution status is good and red when the solution status is bad. Alternatively, other colors may be used. In an illustrative embodiment, the solution indicator 315 is controlled based on results of the monitoring performed using the one or more solution sensor(s) 320 and/or the status of the timer 335 used to monitor shelf life of the solution. Activation and use of the solution indicator 315 is described in more detail with reference to the examples below.

The motion sensor 340 can include any type of movement sensing technology known in the art. The motion sensor 340 can be used to detect movement of the vessel 300, which should be indicative of the presence of a user. The motion sensor 340 can therefore be used to activate the solution indicator 315 while a user is present to help preserve the power source 330. For example, in response to the detection of movement of the vessel 300 by the motion sensor 340, the processor 305 can activate the solution indicator 315 (e.g., as a green light) to indicate that the solution in the vessel is still good. Alternatively, the processor 305 can activate the solution indicator 315 (e.g., as a red light) to indicate that the solution in the vessel is no longer usable and should be replaced. In one embodiment, the solution indicator 315 can be activated for a predetermined amount of time after the movement is detected by the motion sensor 340, such as 10 seconds, 30 seconds, 1 minute, 2 minutes, 5 minutes, etc.

In one embodiment, the vessel 300 can be configured such that the solution indicator 315 is only activated in response to motion after a predetermined amount of time has passed since the last activation of the solution indicator 315 or the last movement detected by the motion sensor 340. As an example, the motion sensor 340 can detect motion, and the solution indicator 315 can be activated for a predetermined duration of time after the detected movement to inform the user of the solution status. The user may continue to periodically move the vessel 300 while using it over a period of 30 minutes. In an effort to conserve the power source 330 of the vessel 300, the processor 305 can ensure that the solution indicator 315 is only activated a single time during the 30 minutes that the vessel 300 is being used. Once the use (and the motion) ceases, the processor 305 can use a timer to ensure that an inactivity period has passed prior to re-activating the solution indicator 315. The inactivity period can be 10 minutes, 15 minutes, 1 hour, 2 hours, etc. In an alternative embodiment, the processor 305 can start a timer when the solution indicator 315 is activated to ensure that the solution indicator 315 is only activated once within a given time period such as 10 minutes, 15 minutes, 1 hour, 2 hours, etc. In such an embodiment, re-activation of the solution indicator 315 can be responsive to both expiration of the predetermined time period since the last activation and subsequent movement detected by the motion sensor 340.

In another embodiment, the motion sensor 340 can be used to monitor and/or track use of the vessel 300 to help ensure that a user is doing his/her job properly. In such an embodiment, the vessel 300 can store data regarding the time/duration of detection movement in the memory 310. An administrator can access the stored data to monitor use of the vessel 300 and to determine if the vessel 300 is being used at the appropriate time(s) and/or an appropriate number of times over a given time period. In one embodiment, the vessel can also include a location tracking sensor that can determine the location of the vessel 300 throughout a day, week, etc. The location tracking sensor can be a global positioning system (GPS) sensor, a radio frequency (RF) sensor, a wi-fi tag, and/or any other location detecting sensor(s) known in the art. In such an embodiment, location information regarding the vessel 300 can also be stored in the memory 310.

The user interface 345 of the vessel 300 can include a display, one or more buttons, a keypad, and/or any other components that allow a user or administrator to interact with the vessel. The user interface 345 can allow the user to adjust default thresholds, reset the vessel 300, assign a vessel ID, program the vessel 300, etc. In one embodiment, the user interface 345 can be remotely accessible through an app or other program on a user device such as a smartphone or computer. The app or other program can communicate with the vessel via the transceiver 325. In an alternative embodiment, the vessel 345 may be pre-programmed and may not include a user interface.

The vessel head 350 of the vessel is used to apply the solution from the vessel 300 to a surface. The vessel head 350 can be a trigger sprayer, a pump sprayer, a squeeze hole, an applicator, and/or other dispensing mechanism known in the art. Alternatively, the vessel may be a type of container (e.g., a bucket) that does not include a vessel head. The reservoir 355 can be any type of receptacle that is able to hold the solution. In an illustrative embodiment, the one or more solution sensor(s) 320 may be placed within the reservoir 355 such that one or more sensor electrodes are in contact with the solution for taking measurements.

As discussed above, the one or more solution sensor(s) 215 of the filling station 200 and the one or more solution sensor(s) 320 of the vessel 300 can be electrical sensors that are used to test/monitor temperature, conductivity, amperage, voltage, and/or amperage at specific chemical reaction potentials (i.e., voltages) of a solution. As discussed in more detail below, the sensors can be used to perform voltammetry such as linear sweep voltammetry, staircase voltammetry, square wave voltammetry, cyclic voltammetry (i.e., a voltammetric method that can be used to determine diffusion coefficients and half cell reduction potentials), anodic stripping voltammetry (i.e., a quantitative, analytical method for trace analysis of metal cations in which an analyte is deposited (electroplated) onto the working electrode during a deposition step, and then oxidized during a stripping step at which time the current is measured), cathodic stripping voltammetry (i.e., a quantitative, analytical method for trace analysis of anions in which a positive potential is applied, oxidizing a mercury electrode and forming insoluble precipitates of the anions, and in which a negative potential then reduces (strips) the deposited film into solution), adsorptive stripping voltammetry (i.e., a quantitative, analytical method for trace analysis in which an analyte is deposited by adsorption on an (chemically modified) electrode surface without electrolysis and electrolyzed to provide an analytical signal), alternating current voltammetry (i.e., potentiodynamic electrochemical impedance spectroscopy), polarography (i.e., a subclass of voltammetry where the working electrode is a dropping mercury electrode (DME) that is useful for its wide cathodic range and renewable surface), rotated electrode voltammetry (i.e., a hydrodynamic technique in which the working electrode, usually a rotating disk electrode (RDE) or rotating ring-disk electrode (RRDE), is rotated at a very high rate, which is useful for studying the kinetics and electrochemical reaction mechanism for a half reaction), normal pulse voltammetry, differential pulse voltammetry, and/or chronoamperometry. Included below are several examples of how the sensors are used in vessel system embodiments to help ensure that a solution is usable for its intended purpose.

In one example embodiment, the vessel system can solely utilize a shelf life timer to determine whether a solution placed into a vessel is still usable. The sole use of a shelf life timer may be appropriate for certain types of solutions such as cleaning solutions and non-oxidizer disinfecting solutions in which chemical decay, in and of itself, is not a major concern. Cleaning solutions are typically very dilute and include little or no preservative ingredients, which makes them susceptible to bacterial growth. Such bacterial growth can cause the solution to become unhygienic. Non-oxidizer disinfecting solutions are typically self-preserving and can have a relatively long shelf life. For both cleaning solutions and non-oxidizer disinfecting solutions, the shelf life can be solution specific and can be based on solution type, solution concentration, the environment in which the solution is used or stored, etc. In one embodiment, a standardized preservation test score for the solution can be used to determine the shelf life period.

In such an embodiment that utilizes a shelf life timer, a user fills a vessel by removing the vessel head (if present) from the vessel and placing the vessel on a docking station or pad of the filling station. The filling station communicates with the vessel to determine a Vessel Identifier (ID) and Solution Type associated with the vessel. The filling station also uses a conductivity sensor within the vessel to determine whether the vessel is empty. In an alternative embodiment, the filling station can determine whether the vessel is empty based on a mass of the vessel and/or any other techniques. In an illustrative embodiment, the filling station is configured to prevent the vessel from being filled if the vessel has old solution therein.

If the filling station determines that the vessel is empty, the filling station can enable a product dispense button on the filling station. The user can press or otherwise activate the product dispense button to begin filling the vessel with solution. Responsive to filling the vessel, the filling station can reset the shelf life timer on the vessel. In some embodiments, the filling station can also determine the shelf life for the solution and provide the shelf life to the vessel such that the vessel can activate the solution indicator (e.g., a red indicator light) to indicate that the solution should be replaced upon expiration of the shelf life. The shelf life can be specific to the type of solution being placed in the vessel and may be based on environmental conditions in which the vessel is expected to be stored or used. In one embodiment, the solution indicator can also be activated for a period of time responsive to the filling of the vessel to indicate that the solution is in good condition (e.g., a green indicator light). The period of time can be 1 minute, 2 minutes, 5 minutes, etc. Once filled, the user can mount the vessel head back onto the vessel.

During use, the vessel may be configured to activate the solution indicator for a short period of time responsive to detected movement of the vessel. If the timer indicates that the shelf life has not passed, the vessel solution indicator can indicate that the solution is in good condition, or still usable. If the timer indicates that the shelf life is expired, the solution indicator indicates that the solution is no longer usable. Responsive to an indication that the solution is no longer usable, the user should properly dispose of any remaining solution in the vessel and then begin the refill process as discussed above.

In another example embodiment, the vessel system can monitor solution quality in real-time to determine whether the solution is still suitable for use. The real-time solution monitoring can be performed alone or in combination with a shelf life timer as discussed above. In an illustrative embodiment, the real-time solution monitoring is performed for oxidizer disinfection solutions that have an active chemical (e.g., hypochlorite, hydrogen peroxide, etc.) that is known to decay over time. The chemical decay can be difficult to predict because it is affected by many factors that can be difficult to control/predict, such as temperature, UV light exposure, an amount of metal ion traces in the solution, the presence of organic matter in the solution, etc. As a result, the sole use of a shelf life timer for an oxidizer disinfection solution may be ineffective. In alternative embodiments, the real-time solution monitoring can also be used to monitor a cleaning solution and/or a non-oxidizer disinfection solution.

A first operation in performing real-time solution monitoring is to perform measurements on the water (or other liquid) that is used to form the solution. The water can be used as a dilute added to a chemical concentrate (or vice versa), or as part of an electrolysis process that is used to form the solution. The water may include minerals, metals, organic materials, etc. that can create a noise signal and affect the subsequent solution measurements, which are described below. The measurement performed on the water is a reference measurement that can be used to compensate for the noise signal during the subsequent measurements of the solution. In an illustrative embodiment, the water is measured at/by the filling station prior to the introduction of any chemicals or other additives. The results of the water measurement can be stored at the filling station and also in the memory of the vessel such that the measurements can be used for setpoint (i.e., an active chemistry level threshold) determination and correction.

A second operation in performing the real-time solution monitoring is to measure the water plus the chemical(s), etc. that have been introduced to the water to form the solution, either by dilution or an electrolysis process. In the case of electrolysis, the chemical introduced into the water can include both converted (e.g., hypochlorite) and unconverted (e.g., chloride) products. In an illustrative embodiment, this second measurement is a reference measurement that also takes place at the filling station prior to placement of the solution into the vessel. The result of the measurement can be stored at the filling station and also in the memory of the vessel for use in setpoint determination and correction.

In the event that the filling station is an on-site chemistry generator, the first and second reference measurements discussed above can also be used to monitor the quality of the electrolytic cell, in addition to key process parameters such as pH, conductivity, and oxidation reduction potential (ORP) to help ensure that the solution generation process is safely performed. The first and second reference measurements also enable solution concentration control during the dispensing process to help avoid product overdosing and underdosing. In the event that the solution is manufactured as a ready to use solution, the first and second reference measurements can be used during manufacturing to monitor the quality of the solution production process.

A third operation in performing the real-time solution monitoring is to conduct measurements directly after the solution has been placed into the vessel and also periodically (or randomly) over time. This series of third measurements can be performed at/by the vessel. The third measurements are used in conjunction with the above-discussed first and second reference measurements to determine the actual concentration level of the disinfectant in the solution. Each of the third measurements is compared to a threshold (or setpoint) which represents the lowest acceptable concentration (or other characteristic) for the disinfectant or other chemical. The threshold can be a specific concentration value, a value of a relative change in concentration relative to a starting concentration, a change in or specific value of conductivity, a change in or specific value of a voltammetry profile, a change in or specific value of a chronoamperometry profile, etc. If the vessel determines that the measured concentration is below the concentration threshold, the solution indicator is activated to inform the user that the solution should be replaced.

The above-described first, second, and third measurements can be conductivity measurements, voltammetry measurements, and/or chronoamperometry measurements. The measurement techniques can be used alone or in combination with one another. The sensors used to conduct the measurements can be formed using screen printed electrode technology to enable measurements within the vessel. The sensor electrodes can be formed from gold, platinum, glassy carbon, and/or any other suitable materials known in the art. Also, in addition to performing the three sets of measurements described herein, sensors can also be used to measure pH of the solution, to determine quality of an electrolytic cell used to generate the solution, to measure UV light exposure via spectrophotometry, etc.

As an example, the first reference measurement can be a conductivity measurement of the water (or other liquid) in the filling station. The second reference measurement can be a conductivity measurement of the water and the chemical(s) introduced into the water at the filling station. The third measurements can be conductivity measurements of the solution in the vessel. During decay of the disinfectant chemical (e.g., from hypochlorite to chloride ions in the case of chlorine solutions), the conductivity of the solution changes. When a predetermined conductivity change has occurred or when a conductivity threshold has been exceeded, the vessel can activate the solution indicator to inform the user that the solution should be replaced. In an illustrative embodiment, the conductivity measurements can be temperature compensated as known in the art. The conductivity measurements can be conducted using a temperature sensor, one or more conductivity sensors, one or more voltage sensors, one or more current sensors, and/or one or more resistance sensors.

As another example, the first, second, and third measurements of the solution can be voltammetry measurements based on cyclic voltammetry (CV), linear sweep voltammetry (LSV), and/or step and pulse voltammetry (S&PV). The first measurement can be a CV, LSV, and/or S&PV profile that is compensated for both temperature and pH of the water, and that is determined by scanning the voltage range between the water decomposition potentials and beyond for the water. The second measurement can be a CV, LSV, and/or S&PV profile that is compensated for both temperature and pH of the water and introduced chemical(s) in either a reacted or unreacted state. The second measurement is performed by scanning the voltage range between the water decomposition potentials and beyond for the solution. The third measurements can similarly be temperature and pH compensated CV, LSV, and/or S&PV profile measurements of the solution in the vessel. Over time, the CV, LSV, and/or S&PV profile of the solution will change as the chemical in the solution degrades. When a predetermined profile change has occurred or when a profile threshold has been exceeded, the vessel can activate the solution indicator to inform the user that the solution should be replaced. In an illustrative embodiment, the voltammetry measurements can be conducted using a temperature sensor, a pH meter, one or more conductivity sensors, one or more voltage sensors, one or more current sensors, and/or one or more resistance sensors as known in the art.

As another example, the first, second, and third measurements of the solution can be based on chronamperometry (CA) or chronopotentiometry (CP). The first measurement can be a CA and/or CP profile that is compensated for temperature of the water, and that is determined by scanning the voltage range between the water decomposition potentials, including short chrono measurements at specific predefined potentials for the water. The second measurement can be a CA and/or CP profile that is compensated for temperature of the water and introduced chemical(s) in either a reacted or unreacted state. The second measurement is performed by scanning the voltage range between the water decomposition potentials, including short chrono measurements at specific predefined potentials for the water and added chemical(s). The third measurements can similarly be temperature compensated CA and/or CP profile measurements of the solution in the vessel. Over time, the CA or CP profile of the solution will change as the chemical in the solution degrades. When a predetermined profile change has occurred or when a profile threshold has been exceeded, the vessel can activate the solution indicator to inform the user that the solution should be replaced. In an illustrative embodiment, the CA or CP measurements can be conducted using a temperature sensor, one or more conductivity sensors, one or more voltage sensors, one or more current sensors, one or more potentiometers, and/or one or more resistance sensors as known in the art.

Figure 4:
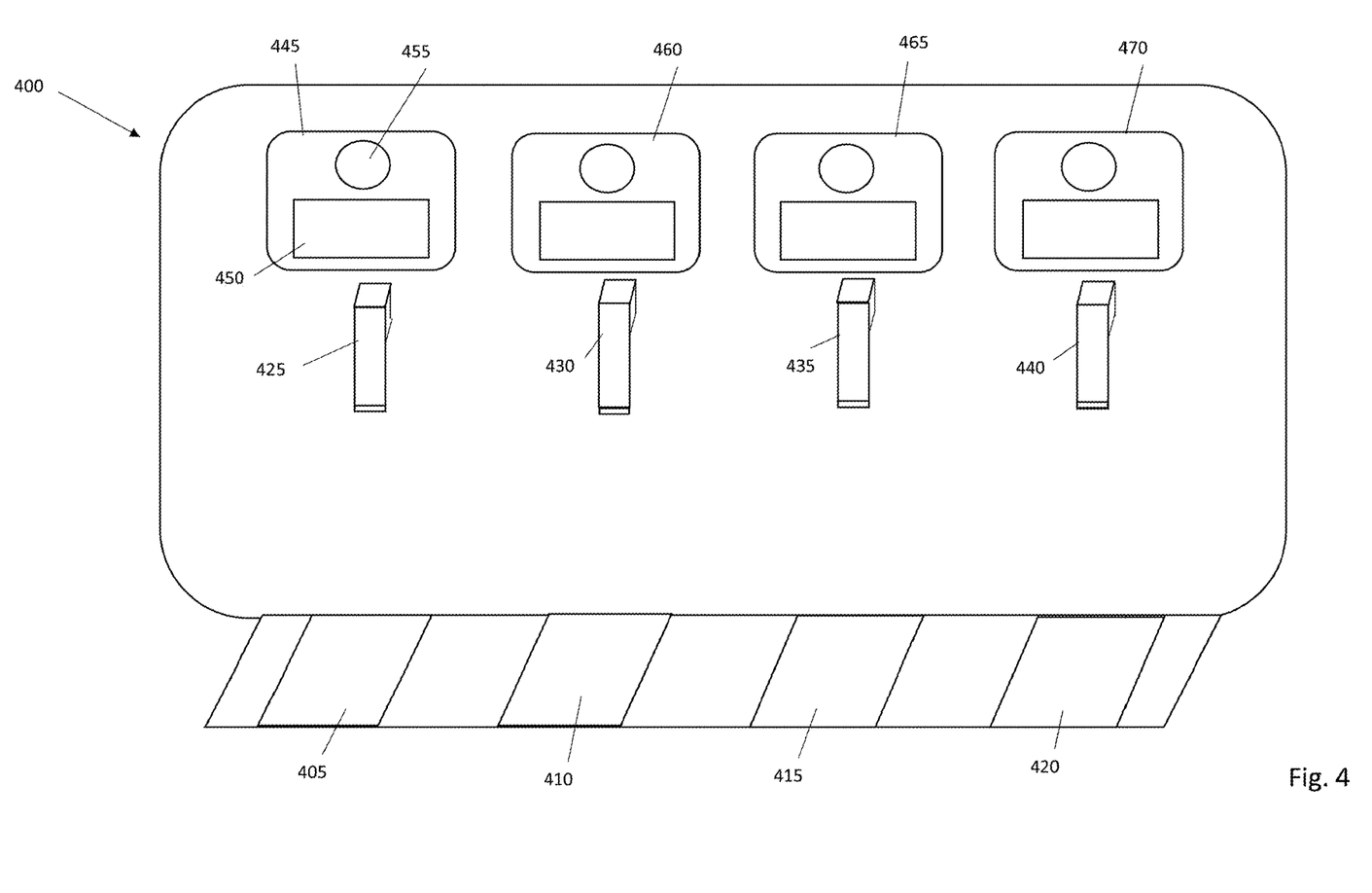
FIG. 4 depicts a filling station in accordance with an illustrative embodiment.

FIG. 4 depicts a filling station 400 in accordance with an illustrative embodiment. The filling station includes a first docking pad (or docking station) 405, a second docking pad 410, a third docking pad 415, and a fourth docking pad 420. In alternative embodiments, fewer or additional docking pads may be used. Each of the docking pads is configured to receive a vessel that is to be filled. In one embodiment, the docking pads can include one or more ports that allow a vessel battery to be charged and/or information to be transferred between the filling station 400 and a vessel. Alternatively, the docking pads may just be designated areas in which a vessel can be placed for a fill operation. In an illustrative embodiment, the fill station is able to wirelessly communicate with a vessel that is positioned at one of the docking pads, as described herein.

Aligned with each of the docking pads 405, 410 415, and 420 is a respective fill nozzle. A first fill nozzle 425 aligns with the first docking pad 405, a second fill nozzle 430 aligns with the second docking pad 410, a third fill nozzle 435 aligns with the third docking pad 415, and a fourth fill nozzle 440 aligns with the fourth docking pad 420. In one embodiment, each of the fill nozzles can be associated with a particular solution such that the fill nozzle only dispenses the particular solution and no others. Alternatively, each of the fill nozzles may be configured to dispense one of a plurality of solutions.

Each of the fill nozzles is associated with an interface. For example, the first fill nozzle 425 is associated with a first interface 445, etc. The first interface 445 includes a display 450 and a dispense button 455. The second, third, and further interfaces 460, 465, and 470 can similarly include a display and dispense button. The display 450 can be an electronic display, a sticker, a plate, etc. that provides information to a user such as the type of solution associated with that docking pad or instructions. For example, if the filling station determines that the vessel placed on the docking pad 405 is not empty, the display 450 may instruct the user to empty the vessel completely prior to attempting a fill operation. The display 450 may also indicate the type of solution and/or characteristics of the solution that is to be placed into the vessel. In one embodiment, the display 450 can include a touchscreen, keypad, or other mechanism through which a user can enter information into the filling station. In an alternative embodiment, the filling station 400 may not include any displays.

The dispense button 450 can be pressed by the user to commence the fill operation. In one embodiment, the display 450 may be incorporated into a face of the dispense button 450. In another embodiment, the dispense button 450 may light up when the filling station 400 is ready for a user to commence the fill operation, such as in response to a determination that the vessel is empty.

Figure 5:
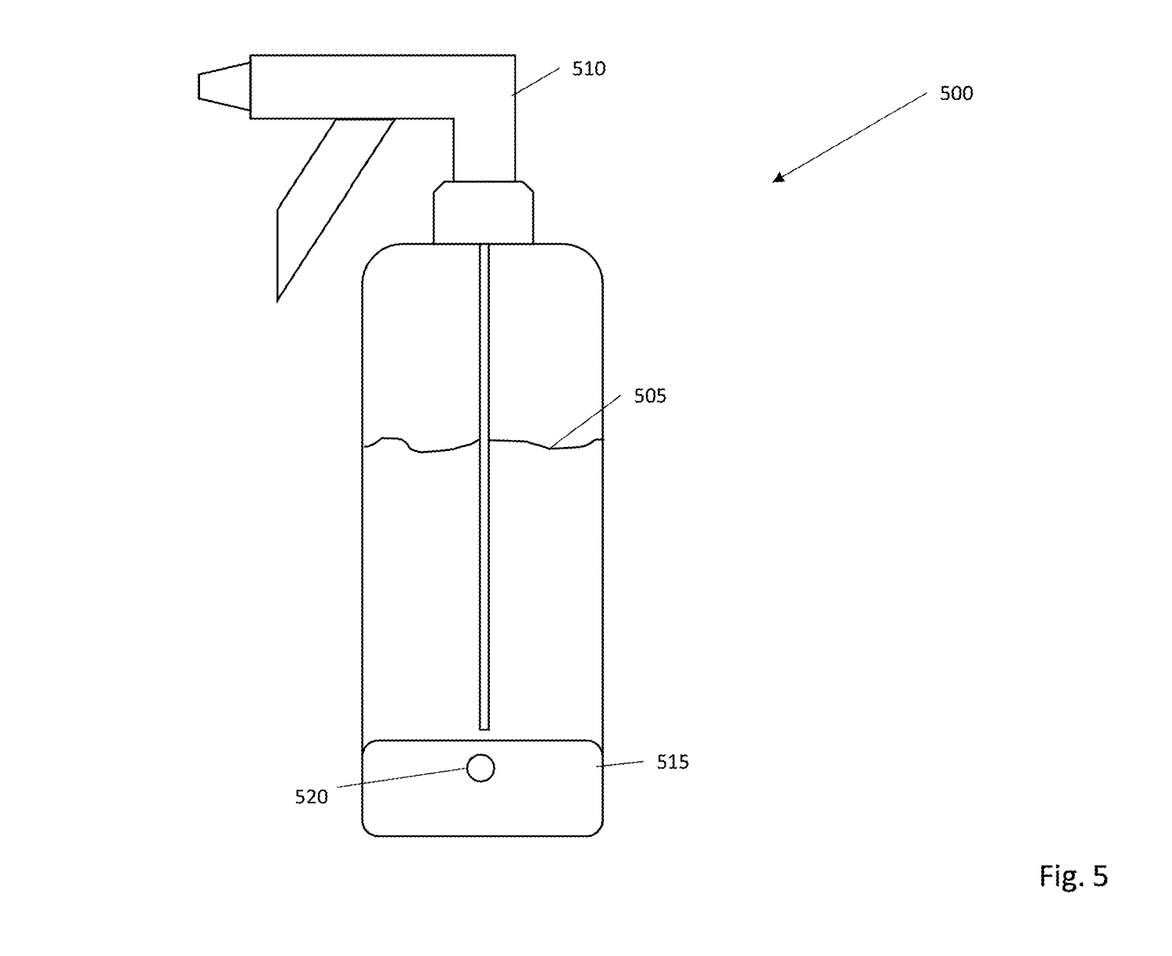
FIG. 5 depicts a vessel in the form of a dispenser in accordance with an illustrative embodiment.

FIG. 5 depicts a vessel in the form of a dispenser 500 in accordance with an illustrative embodiment. The dispenser 500 is in the form of a spray bottle and includes a solution 505 in a reservoir that can be dispensed through a dispensing head 510, which is in the form of a trigger activated spray nozzle. In alternative embodiments, the dispenser 500 can be in any other form and can include a different type of dispensing head. The dispenser 500 also includes an electronics unit 515 that has an incorporated indicator light 520. The electronics unit 515 can include dispenser components such as a processor, a memory, one or more solution sensors, a transceiver, a power source, a timer, a motion sensor, etc. The indicator light 520 can be a solution indicator that is used to inform a user of the status of the solution 505. In one embodiment, the indicator light 520 can display a green light if the solution 505 is still good and a red light if the solution 505 should be replaced. Alternatively, any other type of indicator system may be used. Additionally, although the electronics unit 515 is depicted at a bottom of the dispenser 500, in alternative embodiments the electronics unit 515 may be positioned in the dispensing head 510 or elsewhere within the dispenser 500.

As discussed herein, it is desirable to prevent the use of expired or otherwise ineffective cleaning/disinfecting solutions because the use of such solutions can result in unsanitary conditions. In one embodiment, the dispenser 500 can be configured to prevent use of the solution 505 if the dispenser determines that the solution should not be used due to expiration, degradation, etc. For example, the dispenser 500 can include a solenoid or other mechanical component that prevents actuation of the dispensing head 510 or the pump/tube connected to the dispensing head 510. As an example, upon determining that the solution is no longer good, the electronics unit 515 of the dispenser can activate the solenoid to mechanically prevent further use of the solution. The solenoid can activate a mechanical trigger stop, a mechanical component to block the dispensing tube, a pump block, etc. so that the user is physically unable to dispense the solution. In such an embodiment, the dispenser 500 can remain unusable until the dispenser is filled with fresh solution from a filling station. For example, the processor of the dispenser 500 can control the solenoid or other mechanical component to unlock/activate dispenser responsive to a signal from the filling station indicating that the dispenser has been filled with fresh solution.

In another embodiment, the pump of the dispenser can be an electronic pump that the user activates by pressing a button or other control. Upon determination that the solution in the dispenser is no longer good, the electronics unit 515 of the dispenser 500 can deactivate the electronic pump so that it cannot be used to dispense the solution. The electronic pump of the dispenser can remain deactivated until fresh solution is placed in the dispenser. In some embodiments, upon placement of the fresh solution in the dispenser, the dispenser will automatically reactivate itself. Alternatively, an administrator may also be able to override the deactivation through an interface of the dispenser and/or through a filling station used to fill the dispenser.

As described herein, exposure of a solution to increased temperature can cause solution degradation. In some embodiments, the dispensers described herein can also include one or more temperature sensors that can be used to help monitor the solution. The one or more temperature sensors can monitor the temperature of the solution, which can become elevated if the dispenser is left out in the sun or in an area (e.g., a boiler room) with elevated temperatures. In an illustrative embodiment, the solution can be found unsuitable for use if the monitored temperature ever exceeds a temperature threshold, which can vary depending on the solution. For example, the temperature threshold may be 90° F., 100° F., 110° F., etc. The solution can also be found unsuitable for use if the temperature exceeds a temperature threshold for a designated amount of time. For example, the solution may be considered bad if the temperature of the solution exceeds 105° F. for more than 15 minutes. The specific combination of temperature and time can vary depending on the type of solution.

As also described herein, exposure of a solution to ultraviolet (UV) radiation can cause solution degradation. In some embodiments, the dispensers described herein can also include one or more light sensors that can be used to help monitor the solution. The one or more light sensors can monitor exposure of the solution to ultraviolet rays, and can specifically measure light wavelength and/or intensity (e.g., milliwatts per square centimeter). The solution can be found unsuitable for use if the amount of UV radiation exposure exceeds a threshold, which can vary depending on the solution. For example, the solution may be designated unusable if the intensity of UV radiation ever exceeds a given threshold value. Alternatively, the solution may be designated unusable if the intensity of UV radiation exceeds a given threshold value for a given amount of time. Both the temperature and light sensor(s) can be used in combination with one another to evaluate the solution and/or in combination with other solution monitoring techniques described herein.

As discussed herein, the dispenser system can include a timer, which can have multiple different functions depending on the embodiment. The timer can also be used to determine an amount of time that the dispenser was in actual use in between fill ups. For example, the processor of the dispenser can use the timer to generate timestamps each time a user starts and stops using the dispenser to dispense solution. By analyzing the time stamps, the processor can then determine the total amount of time that the dispenser was in use (i.e., the frequency of use) in between fill ups. The timer can also be used in conjunction with the motion sensor to determine the amount of time that the dispenser was in motion (e.g., being pushed on a cleaning cart, in actual use, etc.) versus the amount of time that the dispenser was stationary in between fill ups. These features can be used to help ensure that employees are actually using the solution and properly doing their jobs.

Figure 6:
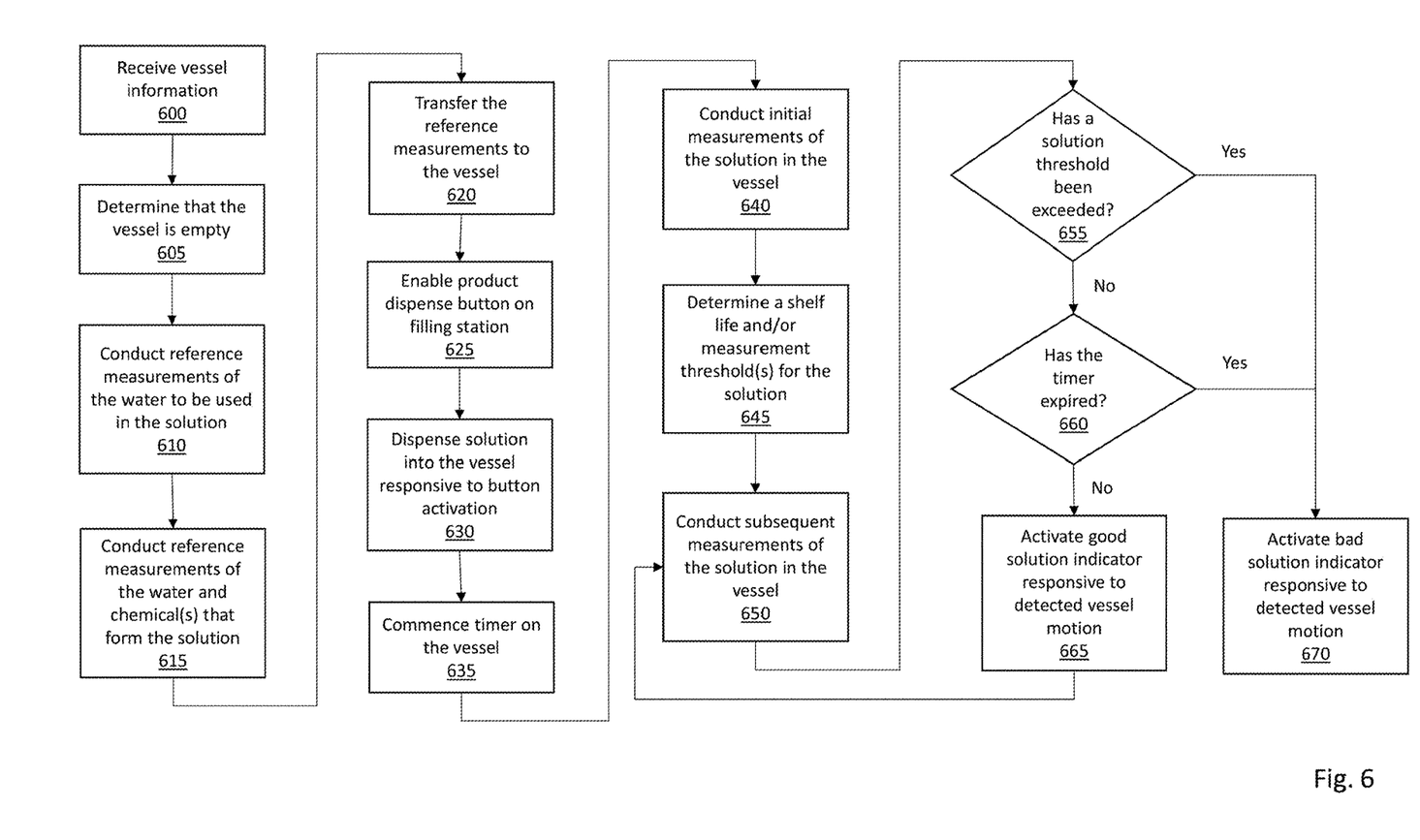
FIG. 6 is a flow diagram depicting operations performed by a vessel system in accordance with an illustrative embodiment.

FIG. 6 is a flow diagram depicting operations performed by a vessel system in accordance with an illustrative embodiment. In alternative embodiments, fewer, additional, and/or different operations may be performed. Also, the use of a flow diagram is not meant to be limiting with respect to the order of operations performed. In an operation 600, a filling station receives vessel information. The vessel information can be received upon placement of the vessel on or near the filling station by a user and via communication between a transceiver of the vessel and a transceiver of the filling station. The vessel information can include a vessel ID and/or information regarding a type of solution that is to be placed into the vessel.

In an operation 605, the filling station determines that the vessel is empty. The determination that the vessel is empty can be based on a conductivity measurement and/or any other type of measurements to determine absence of the solution. In an illustrative embodiment, the filling station can utilize one or more sensors within the vessel to make the determination that the vessel is empty. If it is determined that the vessel is not empty, the filling station can instruct the user to completely empty the vessel prior to attempting a fill operation.

In an operation 610, the filling station conducts reference measurements on the water (or other liquid) that is used to form the solution. In an operation 615, the filling station conducts reference measurements of the water and chemical (s) that form the solution prior to placement of the solution into the vessel. The reference measurements of operations 610 and 615 can be conducted as conductivity measurements, voltammetry measurements, and/or chronoamperometry measurements as described herein. In an operation 620, the reference measurements are transferred to the vessel for use in determining a shelf life for the solution and/or one or more thresholds (or setpoints) related to solution concentration or other characteristic. Alternatively, the filling station can determine the shelf life for the solution and/or the one or more thresholds and transfer that information directly to the vessel. In an alternative embodiment in which just a shelf life is used to monitor the solution, the operations 610-620 may not be performed.

In an operation 625, the filling station enables the product dispense button on the filling station such that the user can commence the dispensing of the solution into the vessel. The filling station can activate a light or other indicator to inform the user that the dispense button has been activated. In an operation 630, the filling station dispenses the solution into the vessel responsive to button activation.

In an operation 635, the timer on the vessel is activated. In an illustrative embodiment, the timer is configured to expire when the determined shelf life for the solution has passed. The shelf life can be 1 day, 2 days, 1 week, 2 weeks, 1 month, etc. depending on the solution and its characteristics. In an operation 640, the vessel conducts initial measurements of the solution in the vessel. In one embodiment, the initial measurements can be performed while the vessel is docked at the filling station such that the measurement data can be transferred to the filling station. Alternatively, the initial measurements can be conducted after the vessel is removed from the filling station. The initial measurements can be conducted as conductivity measurements, voltammetry measurements, and/or chronoamperometry measurements as described herein.

In an operation 645, the vessel (and/or the filling station) determines a shelf life and/or measurement thresholds for the solution based on the first and second reference measurements, the initial measurement of the solution in the vessel, the solution type, environmental information regarding where the solution is to be used/stored, etc. In an alternative embodiment, the shelf life and/or measurement thresholds may be determined prior to commencement of the timer on the vessel. The shelf life and/or measurement thresholds can be determined using any techniques known in the art.

In an operation 650, the vessel conducts subsequent measurements of the solution in the vessel. In an illustrative embodiment, the subsequent measurements can be conducted as conductivity measurements, voltammetry measurements, and/or chronoamperometry measurements, and can be repetitions of the initial measurement(s) made in the operation 640. The subsequent measurements can be conducted on a periodic basis such as once every hour, once every day, once a week, etc. depending on the solution and its characteristics and/or environmental exposure. In the alternative embodiment in which just a shelf life is used to monitor the solution, the operations 640 and 650 may not be performed.

In an operation 655, the vessel determines whether a solution threshold has been exceeded. The determination can be based on the subsequent measurements performed in the operation 650. If it is determined that the solution threshold has not been exceeded, the vessel determines whether the timer has expired in an operation 660. If it is determined that the solution threshold has not been exceeded and that the timer has not expired, the vessel activates a 'good' solution indicator responsive to detected vessel motion in an operation 665. The good solution indicator can, as an example, be a green light, a textual message, or any other positive indicator. The vessel continues to perform operations 650-665 until either the solution threshold is exceeded or the timer expires.

If the vessel determines in the operation 655 that the solution threshold has been exceeded or that the timer has expired in the operation 660, the vessel activates a 'bad' solution indicator in an operation 670. The bad solution indicator can be a red light, a textual message, or any other negative indicator.

Although the vessel systems discussed herein have been described with reference to specific embodiments, it is to be understood that they are not so limited. Rather, the foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

What is claimed is:

1. A vessel system comprising:
   a filling station comprising:
      a filling station transceiver configured to receive a vessel identifier from a vessel; and
      a filling station processor operatively coupled to the filling station transceiver, wherein the filling station processor is configured to:
         conduct a first reference measurement on water used to form a solution using one or more filling station sensors;
         conduct a second reference measurement on the solution prior to placement of the solution in the vessel using the one or more filling station sensors;
         cause the filling station transceiver to transmit data regarding the first reference measurement and the second reference measurement to the vessel; and
         cause a fill nozzle of the filling station to dispense the solution into the vessel; and
   the vessel comprising:
      a vessel memory configured to store the vessel identifier;
      a vessel transceiver configured to transmit the vessel identifier to the filling station and to receive the data regarding the first reference measurement and the second reference measurement; and
      a vessel processor operatively coupled to the vessel memory and the vessel transceiver, wherein the vessel processor is configured to:
         initiate a timer for a shelf life of the solution placed into the vessel;
         conduct a measurement of the solution using one or more vessel sensors;
         compare the measurement to a threshold for the solution; and
         activate a solution indicator to indicate that the solution should be discarded responsive to a determination that the shelf life of the timer has expired or that the measurement exceeds the threshold.

2. The vessel system of claim 1, wherein the vessel processor is further configured to determine the shelf life based at least in part on the data regarding the first reference measurement and the second reference measurement.

3. The vessel system of claim 1, wherein the vessel processor is further configured to determine the threshold based at least in part on the data regarding the first reference measurement and the second reference measurement.

4. The vessel system of claim 1, wherein the filling station processor causes the fill nozzle of the filling station to dispense the solution into the vessel responsive to a determination that the vessel is empty.

5. The vessel system of claim 1, further comprising a motion sensor operatively coupled to the vessel processor, wherein activation of the solution indicator is responsive to movement of the vessel detected by the motion sensor.

6. The vessel system of claim 5, wherein the vessel processor is configured to activate the solution indicator to indicate that the solution is still usable responsive to a determination that the shelf life has not expired, responsive to a determination that the measurement does not exceed the threshold, and responsive to movement detected by the motion sensor.

7. The vessel system of claim 1, wherein the measurement of the solution comprises at least one of a conductivity measurement, a voltammetry measurement, and a chronoamperometry measurement.

8. The vessel system of claim 1, wherein the filling station processor is further configured to activate a dispense button responsive to a determination that the vessel is empty.

9. A vessel system comprising:
a filling station comprising:
  a filling station transceiver configured to receive a vessel identifier from a vessel; and
  a filling station processor operatively coupled to the filling station transceiver, wherein the filling station processor is configured to:
    conduct a first reference measurement on water used to form a solution using one or more filling station sensors;
    conduct a second reference measurement on the solution prior to placement of the solution in the vessel using the one or more filling station sensors;
    determine one of a shelf life or a threshold based at least in part on the data regarding the first reference measurement and the second reference measurement;
    cause the filling station transceiver to transmit data regarding one of the shelf life or the threshold to the vessel; and
    cause a fill nozzle of the filling station to dispense the solution into the vessel; and
the vessel comprising:
  a vessel memory configured to store the vessel identifier;
  a vessel transceiver configured to transmit the vessel identifier to the filling station and to receive the data regarding one of the shelf life or the threshold; and
  a vessel processor operatively coupled to the vessel memory and the vessel transceiver, wherein the vessel processor is configured to:
    if the vessel receives data regarding the shelf life, initiate a timer for the shelf life of the solution placed into the vessel;
    if the vessel receives data regarding the threshold, conduct a measurement of the solution using one or more vessel sensors and compare the measurement to the threshold for the solution; and
    activate a solution indicator to indicate that the solution should be discarded responsive to a determination that the shelf life of the timer has expired or that the measurement exceeds the threshold.

10. The vessel system of claim 9, wherein the filling station processor causes the fill nozzle of the filling station to dispense the solution into the vessel responsive to a determination that the vessel is empty.

11. The vessel system of claim 9, further comprising a motion sensor operatively coupled to the vessel processor, wherein activation of the solution indicator is responsive to movement of the vessel detected by the motion sensor.

12. The vessel system of claim 11, wherein the vessel processor is configured to activate the solution indicator to indicate that the solution is still usable responsive to a determination that the shelf life has not expired, responsive to a determination that the measurement does not exceed the threshold, and responsive to movement detected by the motion sensor.

13. The vessel system of claim 9, wherein the measurement of the solution comprises at least one of a conductivity measurement, a voltammetry measurement, and a chronoamperometry measurement.

14. The vessel system of claim 9, wherein the filling station processor is further configured to activate a dispense button responsive to a determination that the vessel is empty.

\* \* \* \* \*